(12) United States Patent
Allen

(10) Patent No.: US 8,535,341 B2
(45) Date of Patent: *Sep. 17, 2013

(54) METHODS FOR ULTRASONIC TISSUE SENSING AND FEEDBACK

(75) Inventor: Charles D. Allen, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 58 days.

This patent is subject to a terminal disclaimer.

(21) Appl. No.: 13/238,362

(22) Filed: Sep. 21, 2011

(65) Prior Publication Data

US 2012/0010604 A1    Jan. 12, 2012

Related U.S. Application Data

(63) Continuation of application No. 12/582,857, filed on Oct. 21, 2009, now Pat. No. 8,038,693.

(51) Int. Cl.
A61B 17/32    (2006.01)

(52) U.S. Cl.
USPC .......................................................... 606/169

(58) Field of Classification Search
USPC ........................................... 604/22; 606/169
See application file for complete search history.

(56) References Cited

U.S. PATENT DOCUMENTS

| | | |
|---|---|---|
| D223,367 S | 4/1972 | Kountz |
| 3,794,236 A | 2/1974 | Salzer et al. |
| D263,020 S | 2/1982 | Rau, III |
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| 5,190,517 A | 3/1993 | Zieve et al. |
| D354,218 S | 1/1995 | Van de Peer |
| 5,449,370 A | 9/1995 | Vaitekunas |
| 5,733,281 A | 3/1998 | Nardella |
| 5,873,873 A | 2/1999 | Smith et al. |
| 5,947,984 A | 9/1999 | Whipple |
| 5,980,510 A | 11/1999 | Tsonton et al. |
| 6,004,335 A | 12/1999 | Vanitekunas et al. |
| D424,693 S | 5/2000 | Pruter |
| D424,694 S | 5/2000 | Tetzlaff et al. |
| D425,201 S | 5/2000 | Tetzlaff et al. |
| 6,063,098 A | 5/2000 | Houser et al. |
| 6,068,647 A | 5/2000 | Witt et al. |
| D449,886 S | 10/2001 | Tetzlaff et al. |

(Continued)

FOREIGN PATENT DOCUMENTS

| CN | 1103807 | 6/1995 |
|---|---|---|
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Ryan Severson

(57) ABSTRACT

An ultrasonic surgical instrument is presented including an ultrasonic transmission member having a proximal end and a distal end, and a handle member located at the proximal end of the transmission member. The ultrasonic surgical instrument also includes an end effector assembly located at the distal end of the transmission member. The end effector assembly includes a sensing mechanism for sensing load variations on tissue based on mechanical vibrations detected on one or more portions of the surgical instrument, the mechanical vibrations sensed by a laser interferometer.

20 Claims, 10 Drawing Sheets

(56) References Cited

U.S. PATENT DOCUMENTS

| | | |
|---|---|---|
| 6,352,532 B1 | 3/2002 | Kramer et al. |
| D457,958 S | 5/2002 | Dycus et al. |
| D457,959 S | 5/2002 | Tetzlaff et al. |
| 6,454,781 B1 | 9/2002 | Witt et al. |
| 6,458,142 B1 | 10/2002 | Faller et al. |
| D487,039 S | 2/2004 | Webster et al. |
| D496,997 S | 10/2004 | Dycus et al. |
| D499,181 S | 11/2004 | Dycus et al. |
| D525,361 S | 7/2006 | Hushka |
| 7,108,695 B2 | 9/2006 | Witt et al. |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| D564,662 S | 3/2008 | Moses et al. |
| D576,932 S | 9/2008 | Strehler |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| D634,010 S | 3/2011 | DeCarlo |
| 2002/0183774 A1 | 12/2002 | Witt et al. |
| 2006/0079875 A1 | 4/2006 | Faller et al. |
| 2006/0079877 A1 | 4/2006 | Houser et al. |
| 2007/0282333 A1 | 12/2007 | Fortson et al. |
| 2007/0282334 A1 | 12/2007 | Young et al. |
| 2008/0319374 A1 | 12/2008 | Zacharias |
| 2009/0036914 A1 | 2/2009 | Houser |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO2010/035831 | 4/2010 |

OTHER PUBLICATIONS

U.S. Appl. No. 08/483,742, filed Jun. 7, 1995, Roger A. Stern.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.

Anonymous. (1987) Homer Mammalok™ Breast Lesion Needle/Wire Localizer, Namic ® Angiographic Systems Division, Glens Falls, New York, (Hospital products price list), 4 pages.

Anonymous. (1999) MIBB Site Marker, United States Surgical (Sales brochure), 4 pages.

Anonymous. Blunt Tubes with Finished Ends. Pointed Cannula, Popper & Sons Biomedical Instrument Division, (Products Price List), one page, Jul. 19, 2000.

Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.

B. Levy M.D. et al., "Update on Hysterectomy New Technologies and Techniques" OBG Management, Feb. 2003.

B. Levy M.D., "Use of a New Vessel Ligation Device During Vaginal Hysterectomy" FIGO 2000, Washington, D.C.

B. F. Mullan et al., (May 1999) "Lung Nodules: Improved Wire for CT-Guided Localization," Radiology 211:561-565.

B. T. Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991), pp. 148-151.

Bulletin of the American Physical Society, vol. 47, No. 5, Aug. 2002, p. 41.

C. F. Gottlieb et al., "Interstitial Microwave Hyperthermia Applicators having Submillimetre Diameters", Int. J. Hyperthermia, vol. 6, No. 3, pp. 707-714, 1990.

C. H. Dumey et al., "Antennas for Medical Applications", Antenna Handbook: Theory Application and Design, p. 24-40, Van Nostrand Reinhold, 1988 New York, V.T. Lo, S.W. Lee.

Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.

Carus et al., "Initial Experience With the LigaSure™ Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.

Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.

Chung et al., "Clinical Experience of Sutureless Closed Hemorrhoidectomy with LigaSure™" Diseases of the Colon & Rectum, vol. 46, No. 1, Jan. 2003.

Cosman et al., "Methods of Making Nervous System Lesions" In William RH, Rengachary SS (eds): Neurosurgery, New York: McGraw-Hill, vol. III, (1984), pp. 2490-2499.

Cosman et al., "Radiofrequency Lesion Generation and its Effect on Tissue Impedence", Applied Neurophysiology, 51:230-242, 1988.

Cosman et al., "Theoretical Aspects of Radiofrequency Lesions in the Dorsal Root Entry Zone" Neurosurgery 15:(1984), pp. 945-950.

Crawford et al., "Use of the LigaSure™ Vessel Sealing System in Urologic Cancer Surger" Grand Rounds in Urology 1999, vol. 1, Issue 4, pp. 10-17.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline, "Light Key Projection Keyboard" 2004 Advanced Input Systems, located at: <http://www.advanced-input.com/lightkey> last visited on Feb. 10, 2005.

Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al. (1995) "Saline-enhanced RF Ablation: Demonstration of Efficacy and Optimization of Parameters", Radiology, 197(P): 140 (Abstr).

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite-Element Codes to Model Electrical Heating and Non-LInear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol. BME-31, No. 1, Jan. 1984, pp. 28-37.

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, " LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, p. 140 (Abstr).

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.

European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

METHODS FOR ULTRASONIC TISSUE SENSING AND FEEDBACK

CROSS-REFERENCE TO RELATED APPLICATIONS

The present application is a Continuation Application claiming the benefit of and priority to U.S. application Ser. No. 12/582,857, filed on Oct. 21, 2009, which is incorporated herein in its entirety by reference.

BACKGROUND

1. Technical Field

The present disclosure relates to an ultrasonic cutting device and method for sensing, measuring, and adjusting tissue properties. More particularly, the present disclosure relates to an ultrasonic cautery cutting device including a feedback mechanism for automatically adjusting, in real-time, ultrasonic waves applied to tissue.

2. Background of the Related Art

Ultrasonic instruments are effectively used in the treatment of many medical conditions, such as removal of tissue and cauterization of vessels. Cutting instruments that utilize ultrasonic waves generate vibrations with an ultrasonic transducer along a longitudinal axis of a cutting blade. By placing a resonant wave along the length of the blade, high-speed longitudinal mechanical movement is produced at the end of the blade. These instruments are advantageous because the mechanical vibrations transmitted to the end of the blade are very effective at cutting organic tissue and, simultaneously, coagulate the tissue using the heat energy produced by the ultrasonic frequencies. Such instruments are particularly well suited for use in minimally invasive procedures, such as endoscopic or laparoscopic procedures, where the blade is passed through a trocar to reach the surgical site.

For each kind of cutting blade (e.g., length, material, size), there are one or more (periodic) driving signals that produce a resonance along the length of the blade. Resonance results in optimal movement of the blade tip and, therefore, optimal performance during surgical procedures. However, producing an effective cutting-blade driving signal is not a trivial task. For instance, the frequency, current, and voltage applied to the cutting tool must all be controlled dynamically, as these parameters change with the varying load placed on the blade and with temperature differentials that result from use of the tool.

FIG. 1 shows a block schematic diagram of a prior-art circuit used for applying ultrasonic mechanical movements to an end effector. The circuit includes a power source 102, a control circuit 104, a drive circuit 106, a matching circuit 108, a transducer 110, and also includes a handpiece 112, and a waveguide 114 secured to the handpiece 112 (diagrammatically illustrated by a dashed line) and supported by a cannula 120. The waveguide 114 terminates to a blade 116 at a distal end. A clamping mechanism referred to as an "end effector" 118, exposes and enables the blade portion 116 of the waveguide 114 to make contact with tissue and other substances.

The drive circuit 106 produces a high-voltage self-oscillating signal. The high-voltage output of the drive circuit 106 is fed to the matching circuit 108, which contains signal-smoothing components that, in turn, produce a driving signal (wave) that is fed to the transducer 110. The oscillating input to the transducer 110 causes the mechanical portion of the transducer 110 to move back and forth at a magnitude and frequency that sets up a resonance along the waveguide 114.

For optimal resonance and longevity of the resonating instrument and its components, the driving signal applied to the transducer 110 should be as smooth a sine wave as may practically be achieved. For this reason, the matching circuit 108, the transducer 110, and the waveguide 114 are selected to work in conjunction with one another and are all frequency sensitive with and to each other.

Because a relatively high-voltage (e.g., 100 V or more) is required to drive a typical piezoelectric transducer 110, the power source that is available and is used in prior-art ultrasonic cutting devices is an electric mains (e.g., a wall outlet) of, typically, up to 15 A, 120 VAC. Therefore, most ultrasonic cutting devices resemble that shown in FIGS. 1 and 2 and utilize a countertop box 202 with an electrical cord 204 to be plugged into the electric mains 206 for supply of power. Resonance is maintained by a phase locked loop (PLL), which creates a closed loop between the output of the matching circuit 108 and the drive circuit 106. For this reason, in prior art devices, the countertop box 202 includes all of the drive and control electronics 104, 106 and the matching circuit(s) 108. A supply cord 208 delivers a sinusoidal waveform from the box 202 to the transducer 110 within the handpiece 112 and, thereby, to the waveguide 114.

A disadvantage exists in the prior art due to the frequency sensitivity of the matching circuit 108, the transducer 110, and the waveguide 114. By having a phase-locked-loop feedback circuit between the output of the matching circuit 108 and the drive circuit 104, the matching circuit 108 is required to be located in the box 202, near the drive circuit 108, and separated from the transducer 110 by the length of the supply cord 208. This architecture introduces transmission losses and electrical parasitics, which are common products of ultrasonic-frequency transmissions.

In addition, prior-art devices attempt to maintain resonance at varying waveguide 114 load conditions by monitoring and maintaining a constant current applied to the transducer. However, the only predictable relationship between current applied to the transducer 110 and amplitude is at resonance. Therefore, with constant current, the amplitude of the wave along the waveguide 114 is not constant across all frequencies. When prior art devices are under load, therefore, operation of the waveguide 114 is not guaranteed to be at resonance and, because only the current is being monitored and held constant, the amount of movement on the waveguide 114 may vary greatly. For this reason, maintaining constant current is not an effective way of maintaining a constant movement of the waveguide 114.

Furthermore, in the prior art, handpieces 112 and transducers 110 are replaced after a finite number of uses, but the box 202, which is vastly more expensive than the handpiece 112, is not replaced. As such, introduction of new, replacement handpieces 112 and transducers 110 frequently causes a mismatch between the frequency-sensitive components (108, 110, and 112), thereby disadvantageously altering the frequency introduced to the waveguide 114 and the energy applied to tissue. One way to avoid such mismatches is for the prior-art circuits to restrict themselves to precise frequencies. This precision brings with it a significant increase in cost.

SUMMARY

Notwithstanding all these frequency control arrangements, there is a continuing need for improvement in the control of energy delivery to tissue and the determination when tissue treatment has reached an optimal level.

The present disclosure is intended to overcome the drawbacks of other methods by measuring and adjusting the output with load variations. Specifically, an ultrasonic surgical instrument for applying energy to tissue is presented including an ultrasonic transmission member having a proximal end and a distal end. An ultrasonically-actuated cutting element is provided having a tissue contacting surface and is located at the distal end of the transmission member. A clamp member is supported adjacent to the cutting element for clamping the tissue, the clamp member includes a sensing mechanism for sensing load variations on tissue. A handle member is located at the proximal end of the transmission member for moving the clamp member relative to the cutting element and a feedback mechanism for supplying information related to the load variations. An output of the tissue cutting element is adjusted based on the sensed load variations supplied to the feedback mechanism.

The present disclosure further relates to a method for applying energy to tissue, including positioning an ultrasonically-actuated cutting element having a tissue contacting surface at the distal end of a transmission member, positioning a clamp member adjacent to the cutting element for clamping the tissue, and moving the clamp member relative to the cutting element via a handle member located at the proximal end of the transmission member. The method further includes sensing load variations on tissue via a sensing mechanism and supplying information related to the load variations to the ultrasonic surgical instrument via a feedback mechanism operatively coupled to the sensing mechanism. The method further includes adjusting an output of the tissue cutting element based on the sensed load variations supplied from the feedback mechanism.

The present disclosure further relates to an ultrasonic surgical instrument an ultrasonic transmission member having a proximal end and a distal end. The instrument further includes an ultrasonically-actuated cutting element located at the distal end of the transmission member, a clamp member supported adjacent to the cutting element and a handle member located at the proximal end of the transmission member that moves the clamp member relative to the cutting element. The proximal end includes a sensing mechanism that senses load variations and supplies information related to the load variations. An output of the tissue cutting element is adjusted based on the sensed load variations supplied to the feedback mechanism.

Other features that are considered as characteristic for the disclosure are set forth in the appended claims. As required, detailed embodiments of the present disclosure are disclosed herein; however, it is to be understood that the disclosed embodiments are merely examples of the disclosure, which may be embodied in various forms. Therefore, specific structural and functional details disclosed herein are not to be interpreted as limiting, but merely as a basis for the claims and as a representative basis for teaching one of ordinary skill in the art to variously employ the present disclosure in virtually any appropriately detailed structure. Further, the terms and phrases used herein are not intended to be limiting; but rather, to provide an understandable description of the disclosure. While the specification concludes with claims defining the features of the disclosure that are regarded as novel, it is believed that the disclosure will be better understood from a consideration of the following description in conjunction with the drawing figures, in which like reference numerals are carried forward. The figures of the drawings are not drawn to scale.

BRIEF DESCRIPTION OF THE DRAWINGS

Various embodiments of the present disclosure will be described herein below with reference to the figures wherein.

DETAILED DESCRIPTION

Figure 1:
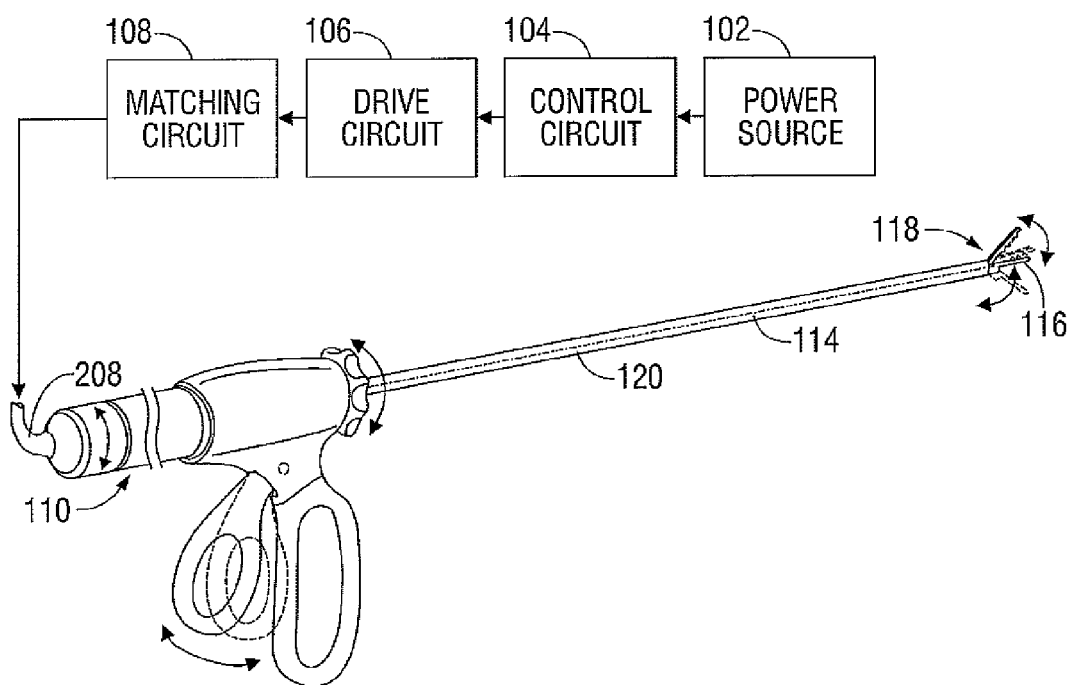
FIG. 1 is an illustration of components of a prior-art ultrasonic cutting device with separate power, control, drive and matching components in block diagram form.
Figure 2:
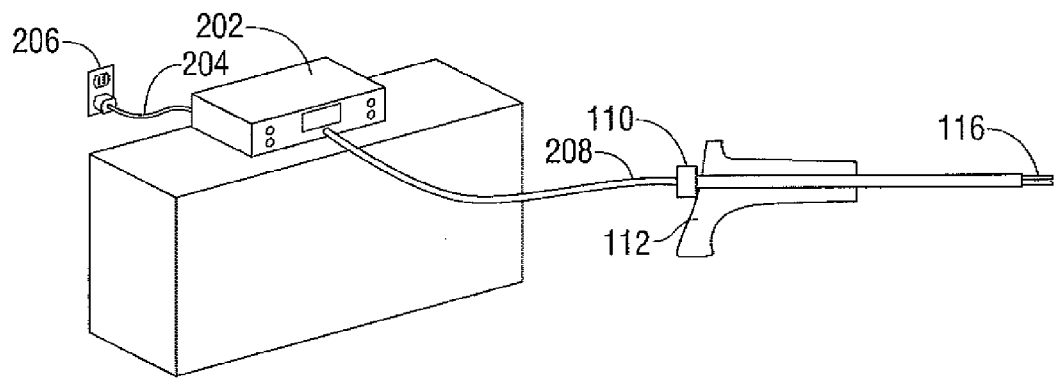
FIG. 2 is a diagram illustrating the prior-art ultrasonic cutting device of FIG. 1.

Particular embodiments of the present disclosure are described hereinbelow with reference to the accompanying drawings. In the following description, well-known functions or constructions are not described in detail to avoid obscuring the present disclosure in unnecessary detail.

It is to be understood that the disclosed embodiments are merely examples of the present disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Further, the terms and phrases used herein are not intended to be limiting; but rather, to provide an understandable description of the present disclosure.

Before the present disclosure is disclosed and described, it is to be understood that the terminology used herein is for the purpose of describing particular embodiments only and is not intended to be limiting. In this document, the terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the object being described.

It will be appreciated that embodiments of the disclosure described herein may be comprised of one or more conventional processors and unique stored program instructions that control the one or more processors to implement, in conjunction with certain non-processor circuits and other elements, some, most, or all of the functions of ultrasonic cutting devices described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could also be used. Thus, methods and means for these functions have been described herein.

The present disclosure, according to one embodiment, overcomes problems with the prior art by providing a light-weight, hand-holdable, ultrasonic cutting device that includes a feedback mechanism for automatically adjusting, in real-time, ultrasonic waves applied to tissue.

Figure 3:
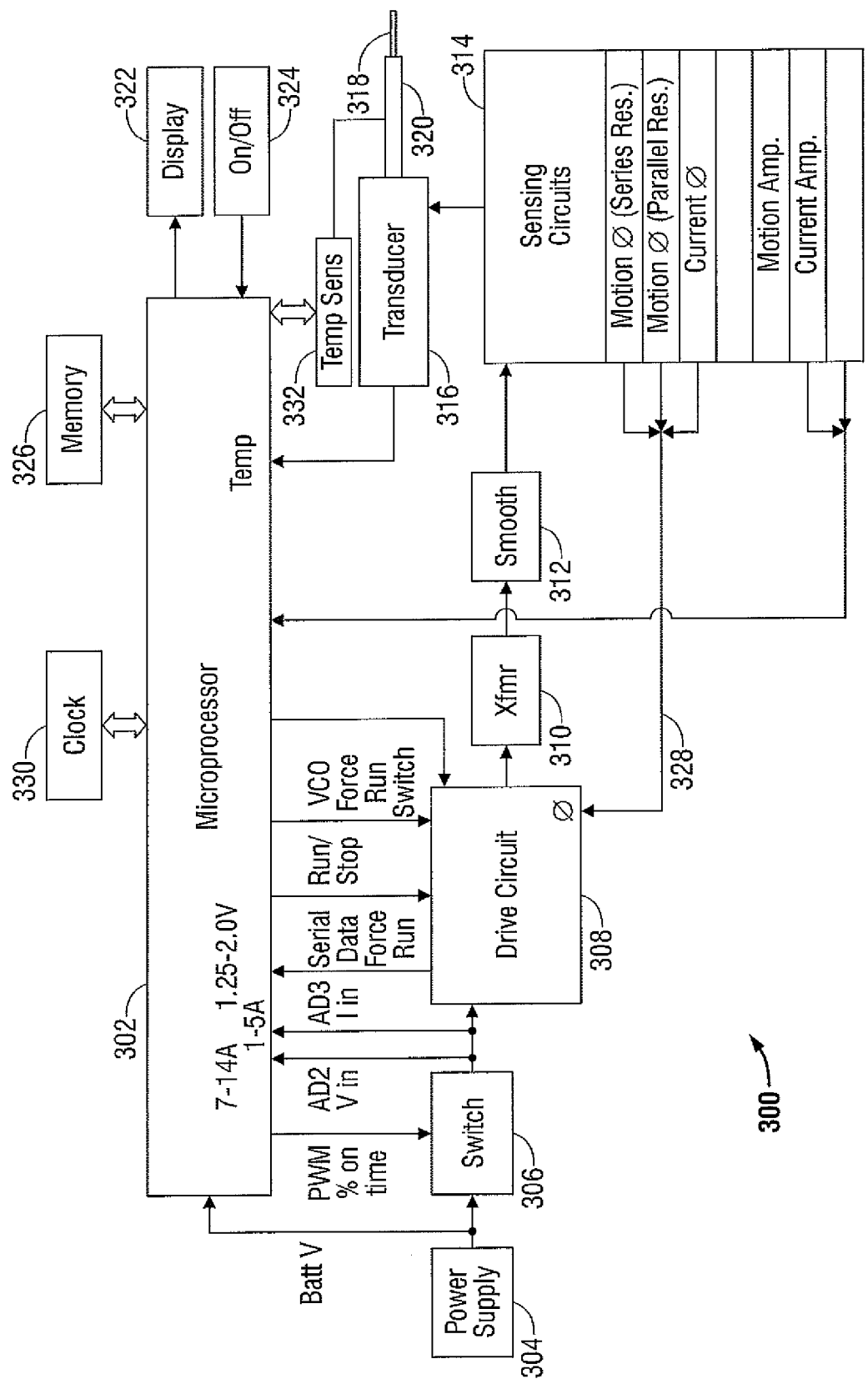
FIG. 3 is a block circuit diagram of an ultrasonic cutting device, in accordance with an example embodiment of the present disclosure.

Referring to FIG. 3, a block circuit diagram 300 is shown, which includes a microprocessor 302, a clock 330, a memory 326, a power supply 304 (e.g., a battery), a switch 306 (e.g., a MOSFET power switch), a drive circuit 308 (PLL), a transformer 310, a signal smoothing circuit 312 (also referred to as a matching circuit), a sensing circuit 314, a transducer 316, and a waveguide, which terminates into an ultrasonic cutting blade 318, referred to herein simply as the waveguide 318. The block circuit diagram 300 also includes a cannula 320 for covering and supporting the waveguide 318. As used herein, the "waveguide-movement-generation assembly" is a sub-assembly including at least the transducer 316, but may also include other components, such as the drive circuit 308 (PLL), transformer 310, signal smoothing circuit 312, and/or the sensing circuit 314. The block circuit diagram 300 also includes a display 322, an on/off switch 324, and a temperature sensor 332.

In operation, the output of the battery 304 is fed to and powers the processor 302. The processor 302 receives and outputs signals and, as is described below, functions according to custom logic or in accordance with computer programs that are executed by the processor 302. The block circuit diagram 300 may also include a main memory 326 that stores computer-readable instructions and data.

The output of the battery 304 is also fed to a switch 306 that has a duty cycle controlled by the processor 302. By controlling the on-time for the switch 306, the processor 302 is able to dictate the total amount of power that is ultimately delivered to the transducer 316. The output of the switch 306 is fed to a drive circuit 308 that contains, for example, a phase detecting PLL and/or a low-pass filter and/or a voltage-controlled oscillator. The output of the switch 306 is sampled by the processor 302 to determine the voltage and current of the output signal (referred to in FIG. 3 respectively as AD2 V In and AD3 I In). These values are used in feedback architectures to adjust the pulse width modulation of the switch 306.

The drive circuit 308, which receives the signal from the switch 306, includes an oscillatory circuit that turns the output of the switch 306 into an electrical signal having a single ultrasonic frequency, e.g., 55 kHz (referred to as VCO in FIG. 3). A smoothed-out version of this ultrasonic waveform is ultimately fed to the transducer 316 to produce a resonant sine wave along the waveguide 318. Resonance is achieved when current and voltage are substantially in phase at the input of the transducer 316. For this reason, the drive circuit 308 uses a PLL to sense the current and voltage input to the transducer 316 and to synchronize the current and voltage with one another. This sensing is performed over line 328.

At the output of the drive circuit 308 is a transformer 310 able to step up the low voltage signal(s) to a higher voltage. It is noted that all upstream switching, prior to the transformer 310, has been performed at low (i.e., battery driven) voltages. This is at least partially due to the fact that the drive circuit 308 advantageously uses low on-resistance MOSFET switching devices.

FIGS. 4 to 8 illustrate various example embodiments of a "gun" type device 1300 suitable to hold and/or contain the components illustrated in FIG. 3. More specifically, as shown in the cutaway view of FIG. 5, the ultrasonic surgical device 1300 includes a disposable ultrasonic cutting tool handle 1408 that has a water-tight sealable battery-holding compartment 1422, a driving-wave generation circuit 1420 in electrical contact with the battery-holding compartment 1422, a transducer attachment dock 1404 accessible from an exterior of the handle and operable to releasably physically couple the transducer 1302 to a waveguide 1310 (represented as a dotted line in FIG. 4) coupled to the handle 1408 through a waveguide attachment dock 1406 that is disposed to accept and physically couple the ultrasonic waveguide 1310 to the transducer 1302.

The ultrasonic surgical device 1300 includes a disposable handle body 1308 defining a battery-holding compartment 1422 shaped to receive a battery 1700 therein and operable to couple a proximal end of the ultrasonic waveguide 1310 to the ultrasonic transducer 1302 therethrough. The handle body 1308 further includes a waveguide attachment dock 1428 shaped to align and attach the proximal end of the waveguide 1310 to the transducer 1302 and thereby hold the waveguide 1310 and the transducer 1302 at least partially within the body when the transducer 1302 is docked in the transducer dock 4102 and the waveguide 1310 is docked in the waveguide attachment dock 1428.

An upper portion of the handle body 1308 houses a disposable driving-wave generation circuit 1420 that is in electrical contact with the battery 1700 and the transducer 1302 when the battery 1700 and transducer are disposed, respectively, in the battery-holding compartment 1422. The generation circuit 1420 is operable to generate an output waveform sufficient to generate ultrasonic movement along the waveguide by exciting the transducer when the transducer is coupled to the waveguide 1310.

The transducer 1302 is generally secured by screwing the transducer 1302 onto a waveguide 1310, both being at least partially within the transducer port 1404. The physical couple between the handle 1408 and the transducer 1302, once attached, may be water-tight and, in some embodiments, may be aseptic. The transducer 1302 imparts the physical forces to the waveguide 1310 at the proper frequency and force and receives power from the battery 1700. The transducer assembly 1302 is shown in greater detail in FIGS. 6 and 7 described below.

Figure 6:
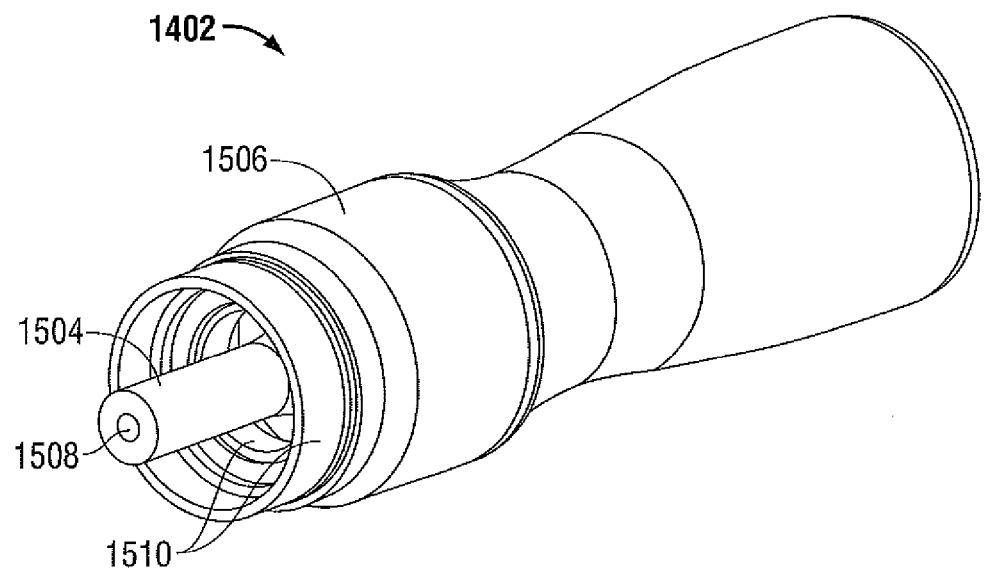
FIG. 6 is a perspective view of a transducer assembly removed from the handle of FIG. 5, in accordance with an example embodiment of the present disclosure.

Referring to FIG. 6, the reusable cordless transducer assembly 1402 is shown separate from the device 1300. The transducer assembly 1402 includes a shaft 1504 with an ultrasonic waveguide couple 1508 that is able to attach to a waveguide and, upon activation of the transducer shaft 1504, excite the attached waveguide, i.e., impart ultrasonic waves along the length of the waveguide. The transducer assembly 1402 also has a housing 1506 that protects and seals the internal working components (see FIG. 7) from the environment. It is advantageous for the transducer assembly 1402 to be selectively removable from the device 1300. As a separate component, the transducer assembly 1402 may be medically disinfected or sterilized, e.g., put in an autoclave, and used for multiple surgeries, while the less-expensive gun itself may be disposable. In addition, the transducer assembly 1402 may be used in multiple guns or in the same gun up to a desired maximum number of times before it is required to be disposed.

Figure 7:
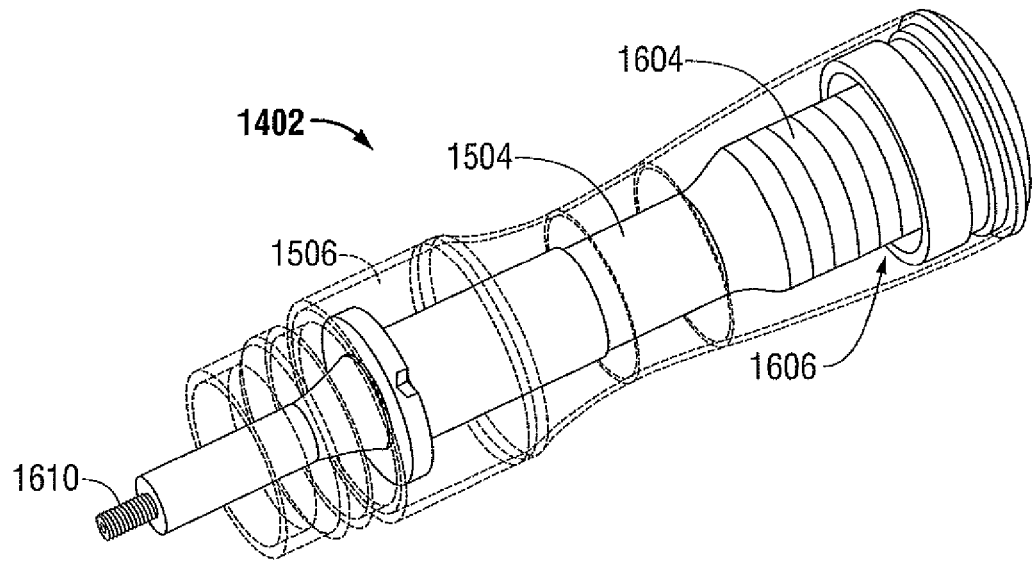
FIG. 7 is a perspective and partially hidden view of the transducer assembly of FIG. 6, in accordance with an example embodiment of the present disclosure.

FIG. 7 shows one example embodiment of the transducer assembly 1302. Within the housing 1506 is the movable shaft 1504. When an electric field is created in the piezoelectric crystal stack 1604 at one end 1606 of the shaft 1504, the shaft 1504 moves laterally within and relative to the housing 1506. In this embodiment, the waveguide coupler 1508 is male and includes threads 1610, which are used to secure the transducer assembly 1302 to the waveguide 1310 by screwing the waveguide 1310 onto the threads 1610 with an appropriate amount of torque. In contrast, in FIG. 6, the waveguide coupler 1508 was female allowing the waveguide to be screwed into the waveguide coupler 1508.

One feature of the transducer 1402 is its ability to mechanically and electrically connect at the same time. FIG. 6 shows an example embodiment of electrical connector rings 1510 of the transducer 1402. As the transducer 1402 is being coupled by the waveguide couple 1508 to a waveguide attached to the handle 1408, the connector rings 1510 are brought into contact with, for example, a set of power contacts (not shown). The power contacts place the piezoelectric crystal stack 1604 in contact with the power source 1700 of the handle 1408. Additionally, the transducer assembly 1302 and the transducer assembly housing 1404 may be sealed so that, in the rare event of surgical fluids contacting the transducer assembly 1302, they do not introduce themselves into the interior of the housing 1506.

Figure 8:
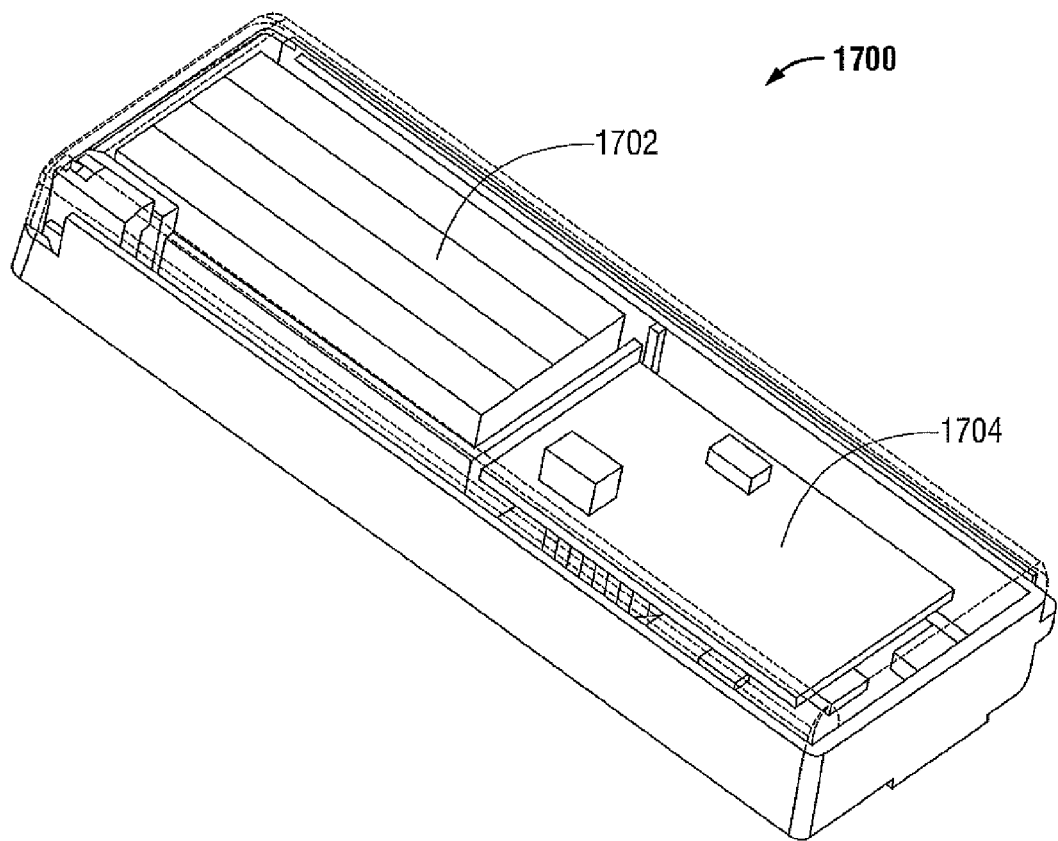
FIG. 8 is a perspective and partially hidden view of the pack shown in the handle of FIG. 5, in accordance with an example embodiment of the present disclosure.

The gun 1300, according to an example embodiment of the present disclosure, has, within its handle 1408, a power assembly 1700 (including power source 1702 and a generator 1704), shown in detail in FIG. 8. The battery 1702 within the power assembly 1700 may be a single battery or a plurality of battery cells operating as a unit.

The battery 1702 powers the generator 1704, which may include some or all of the components shown in FIG. 3 and described in detail above. Specifically, the generator 1704 powers the transducer and includes the processor 302, the switch 306 (e.g., a MOSFET power switch), the drive circuit 308 (PLL), the transformer 310, the signal smoothing/matching circuit 312, and the sensing circuit 314 of FIG. 3.

Figure 5:
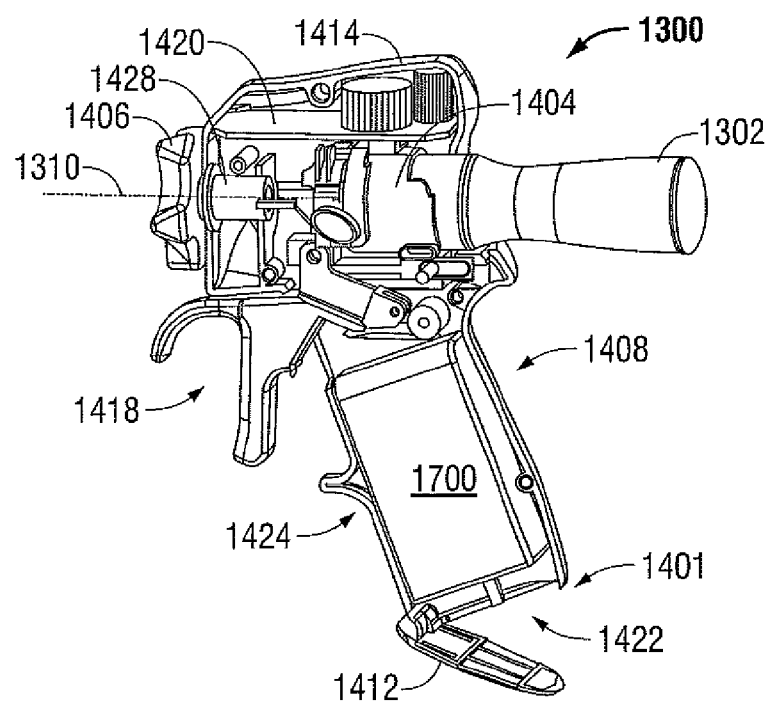
FIG. 5 is a side, elevational view of the handle of FIG. 4 with the left-side shell removed and with the upper slide cover removed to show the integrated control, drive and matching components and removable power supply therein, in accordance with an example embodiment of the present disclosure.

As shown in FIG. 5, for example, the handle 1408 is also provided with a closable door 1412, for instance, at its bottom 1401. This provides a variety of possible assemblies. In one assembly, the gun body 1414, which includes the transducer coupling port 1404 and the triggering mechanisms 1418, is disposable and usually not used more than for a single surgery.

Figure 4:
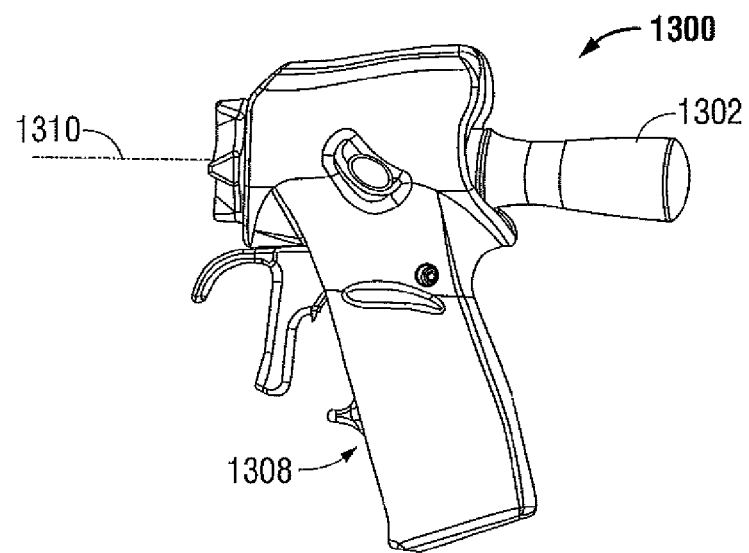
FIG. 4 is a side, elevational view of a left side of an ultrasonic cutting device handle with fully integrated control, drive and matching components and removable transducer and power supply, in accordance with an example embodiment of the present disclosure.

An example procedure for use of the device with the power assembly 1700 is explained with regard to FIGS. 4 and 5. In operation, a person in the sterile field opens a sealed package containing the new sterile gun body 1408 and removes it for use during the operation. The gun body 1408 may either already include the cannula 320 and waveguide 1310 (indicated with a dashed line) or may be coupled to a cannula 320 and waveguide 1310 after the package is opened. Next, the sterile (autoclaved) transducer assembly 1302 is inserted into the gun body 1408 and appropriately attached to the waveguide 1310. The surgeon then presents the underside of the gun body 1408 (with the door 1412 open) to the circulating nurse, who drops the power assembly 1700 into the grip portion 1424 of the gun handle 1408 without contacting the exterior of the gun body 1408. Someone in the operating field (e.g., the surgeon) then closes the door 1412, thereby securing the non-sterile power assembly 1700 within the gun 1300 through a sterile seal 1401 and preventing it from contaminating the sterile field. Because the power assembly 1700 is sealed within the handle 1408, it is "outside" the sterile field during surgery.

Figure 9:
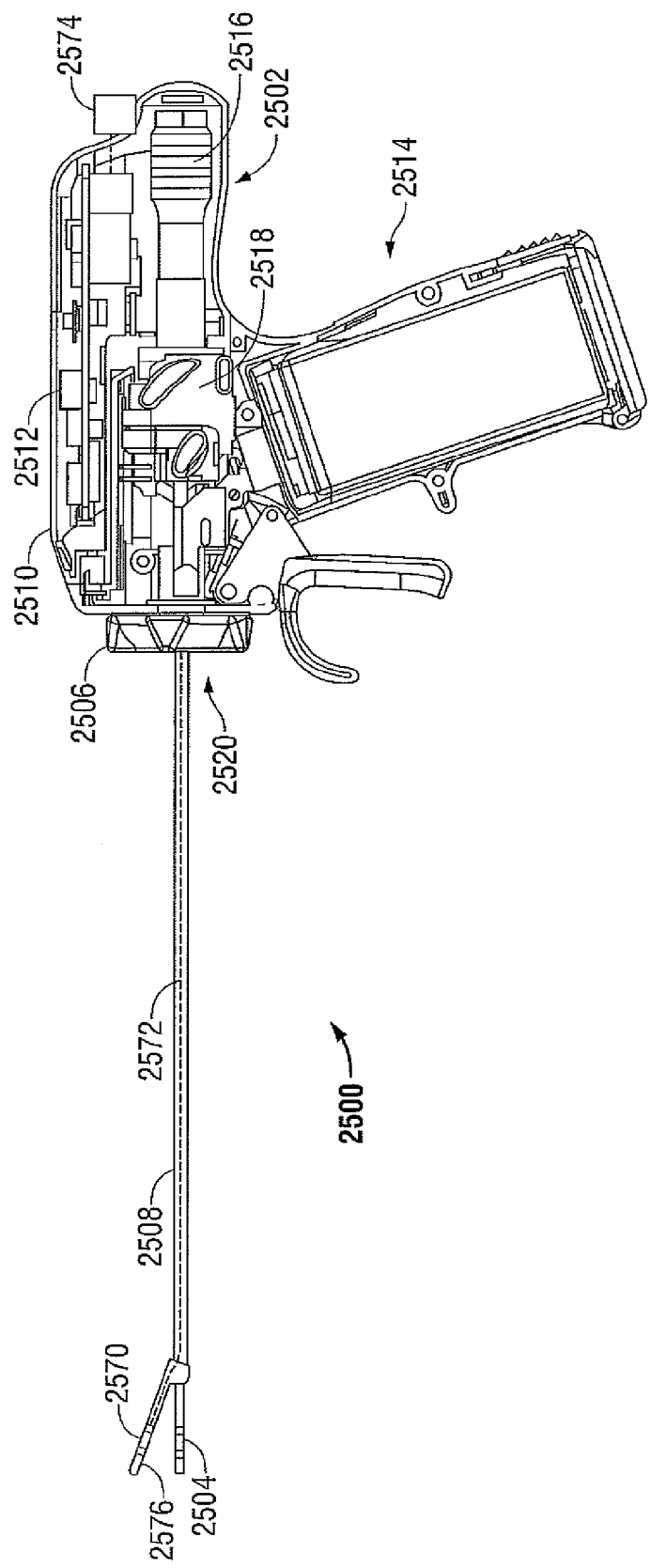
FIG. 9 is a side, elevational view of an handle with the left-side shell removed to show a transducer and generator, a removable power supply, and a blade and waveguide attached to the spindle, in accordance with an example embodiment of the present disclosure.
Figure 10:
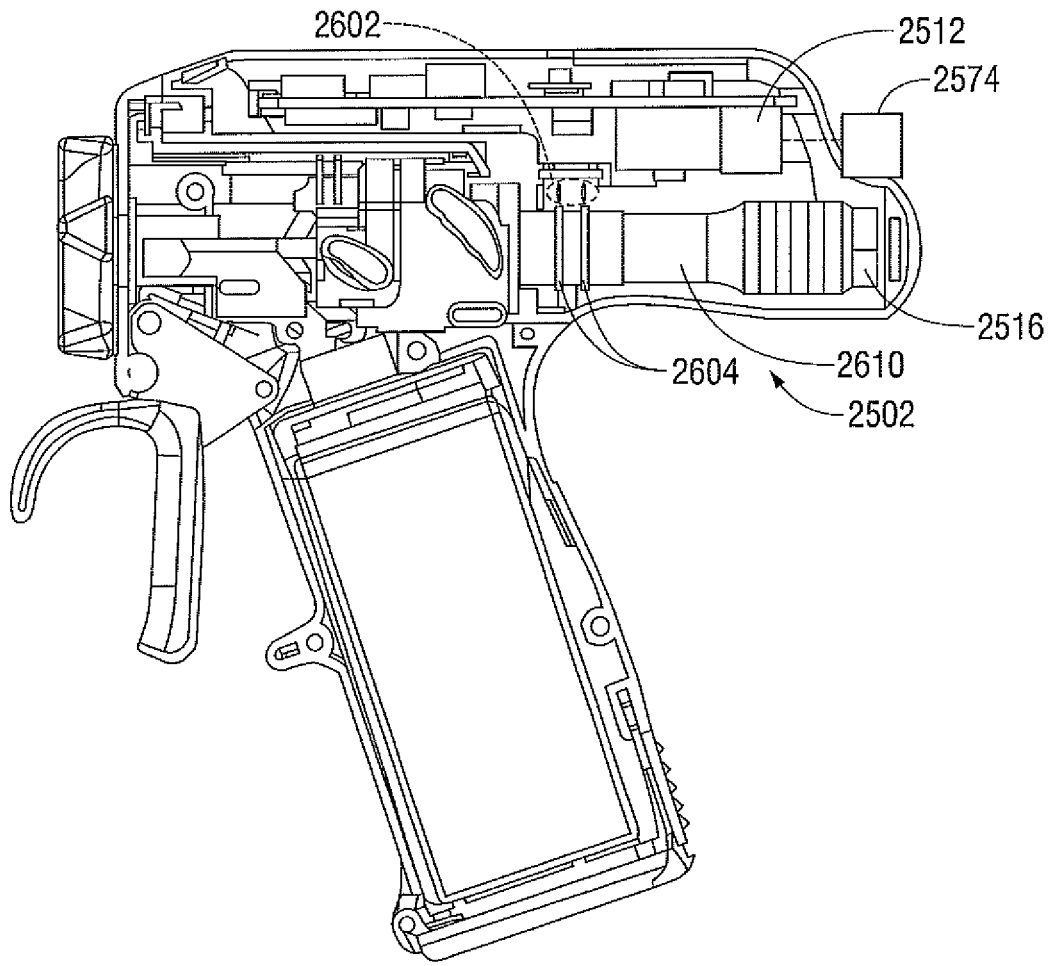
FIG. 10 is a side, elevational view of an handle with the left-side shell removed to show electronic coupling between the generator and transducer assembly of the transducer and generator, in accordance with an example embodiment of the present disclosure.

FIGS. 9-10 show an example embodiment of the present disclosure, which includes a waveguide 2508 with a blade 2504, and includes the transducer and generator, as described above.

Referring now to FIG. 9, when an ultrasonic-movement-generator assembly 2502 is coupled to a handle 2514, the transducer 2516 is caused to be releasably physically coupled to a waveguide 2508 through the transducer attachment port 2518 and waveguide attachment port 2520. It is envisioned that the transducer assembly 2516 may be temporarily locked into a fixed rotational position so that the waveguide 2508 may be attached to the threads 1610 (see FIG. 7) with sufficient force. This physical coupling between the waveguide 2508 and the transducer assembly 2516 allows the transducer assembly 2516 to impart movement to the waveguide 2508 when power is applied to the transducer assembly 2516.

The gun 2500 has a spindle 2506 that attaches to the waveguide 2508. The spindle 2506 has indentions that allow a surgeon to easily rotate the spindle 2506 and, therefore, the attached waveguide 2508 and transducer assembly 2516 that is attached to the waveguide 2508. Such a configuration is useful for obtaining the proper cutting-blade angle during surgery. To provide for this rotation, in one example embodiment, the transducer assembly 2516 is able to rotate freely within the transducer housing 2510.

During initial coupling of the transducer assembly 2516 and waveguide 2508, all that is needed is that one of the transducer assembly 2516 and the waveguide 2508 remains relatively stationary with respect to the other. According to one example embodiment of the present disclosure, when the transducer assembly 2516 is located inside the housing 2510 (where it cannot be readily secured by the operator, for example, by holding it steady by hand when the waveguide 2508 is being secured) the ultrasonic-movement-generator assembly 2502 is provided with a button (not shown) that slides into a recess in the housing 2510 or, alternatively, by fixing the rotation of the transducer assembly 2516 at a maximum rotational angle so that, once the maximum rotation is reached, for example, 360 degrees of rotation, no additional rotation is possible and the waveguide 2508 may be screwed thereon. Of course, a maximum rotation in the opposite direction allows the waveguide 2508 to be removed as well.

FIG. 10 shows one example of how the generator assembly 2512 and transducer assembly 2516 are electrically coupled so that a physical rotation of the transducer assembly 2516 with respect to the generator assembly 2512 is possible. In this example, the generator assembly 2516 has a pair of contacts 2602 protruding from its underside, adjacent the transducer assembly 2516. Proximity of the transducer assembly 2516 to the generator assembly 2512 places one of the pair of contacts 2602 (circled) in physical communication with a pair of contact rings 2604 at the transducer body 2610 so that a driving signal may be steadily applied to the transducer assembly 2516 when needed. Advantageously, the pair of contacts 2602 maintains electrical contact regardless of an angle of rotation of the transducer assembly 2516. Therefore, the transducer assembly 2516 may rotate without any limitations as to the maximum angle or number of rotations.

Referring to FIGS. 4-10, and especially to FIG. 9, the example embodiments of the present disclosure include a feedback mechanism. For instance, a plurality of sensors 2570 (see FIG. 9) may be located at the blade 2504 of the gun 2500. The plurality of sensors 2570 may be connected to a feedback mechanism 2574 via one or more wires 2572 extending from the distal end to the proximal end of the gun 2500. The one or more wires 2572 are positioned within the waveguide 2508. However, one skilled in the art may contemplate an external configuration of wires for linking the plurality of sensors 2570 to the feedback mechanism 2574. The feedback mechanism 2574 may be positioned within the handle 2514 or any other portion of the gun 2500. The feedback mechanism 2574 may even be positioned on an outer portion of the gun 2500.

The feedback mechanism 2574 may be provided to interact with any sensors 2570 provided to enable more effective ligation, cutting, dissection, coagulation, etc. For example, the feedback mechanism 2574 may terminate operation of the gun 2500 if one or more sensors of the plurality of sensors 2570 indicate that tissue temperature or ultrasonic or electrical impedance has exceeded a predetermined maximum. The feedback mechanism 2574 may be selectively activated and deactivated and/or controlled or monitored by a surgeon to provide the surgeon with more flexibility in operating the gun 2500. Activating or exciting the end effector of gun 2500 at ultrasonic frequencies induces longitudinal vibratory movement that generates localized heat within adjacent tissue, facilitating both cutting and coagulating.

The transducer 2516 may be constructed of one or more piezoelectric or magnetostrictive elements in the handle 2514. Vibrations generated by the transducer 2516 are transmitted to the blade 2504 via an ultrasonic waveguide extending from the transducer 2516 to the surgical end effector. The waveguides 2504, 2508 are designed to resonate at the same frequency as the transducer 2516. When a blade 2504 is attached to the transducer 2516, the overall system frequency may be the same frequency as the transducer 2516 itself. However, it is contemplated that the transducer 2516 and the blade 2504 may be designed to resonate at two different frequencies and when joined or coupled may resonate at a third frequency.

The blade 2504 of the gun 2500 operates or vibrates at a frequency of about 55 kHz when no tissue is applied to the tip. When tissue is applied to the tip, the tip or blade 2504 may vibrate at a frequency other than 55 kHz. Such frequency depends on, for example, the thickness of the tissue. Thus, the tissue applies a load to the blade 2504. The load is a variable load that may change as the gun 2500 is used during a surgical procedure. The example embodiments of the present disclosure enable the gun 2500 to determine what is causing the load when the gun 2500 is activated. The load may be caused by a number of variables or parameters. For example, such load varying parameters may include, but are not limited to tissue impedance, tissue type, tissue clarity, tissue compliance, and temperature of the tissue.

The waveguide 2508 or blade 2504 may also include a plurality of sensors 2570 for measuring a number of different variables or parameters, such as, but not limited to temperature of the cutting element, water content in tissue, water motality in tissue, and energy delivery. The sensors 2570 may measure one or more parameters (or variables) associated with the tissue or with the gun 2500 and relay such information back to a controller mechanism (not shown) within the gun 2500 which operatively communicates with other controllers to adjust, in real-time, and in an automatic manner, the one or more sensed and measured parameters based upon the information provided by sensors 2570.

These changes in the movement of the waveguide 2508 and/or blade 2504 are measured and fed back into controllers (not shown) of the gun 2500 to provide for automatic, real-time adjustments of the one or more parameters. Thus, movement, vibration, waves, and/or resonance produced by a plurality of parameters or variables may be continuously measured in real-time (as load differentials) and fed back into the controllers in order to automatically readjust such parameters or variables. Movement, vibration, waves, and/or resonance may be measured on any portion of the gun 2500 and/or on any portion of the tissue applied to the blade 2504. Further, the energy source of the gun 2500 may be responsive to a power control signal of a controller. The feedback mechanism 2574 may be coupled to, or included with, the power controller. The power controller may include at least one electrical switch for selectively controlling the energy supplied to the instrument to coagulate tissue, or to cut tissue, depending on the electrical switch setting. In other words, any type of manual or automatic feedback mechanism 2574 may be envisioned by one skilled in the art.

The controllers may be any type of electrical, or electro-mechanical mechanism that provides additional force on a drive assembly (not shown) to modify/alter/readjust one or more parameters of the blade 2504 or waveguide 2508 of the gun 2500. Thus, in the automated system, the characteristics of the tissue are monitored and adjusted during activation based upon a continually-sensed surgical condition from the sensors 2570 relating to any one or more of a series of tissue or waveguide parameters (e.g., tissue impedance, tissue type, tissue clarity, tissue compliance, temperature of the tissue or jaw members, water content in tissue, jaw opening angle, water motality in tissue, energy delivery, etc.) utilizing an open or closed feed back control loop.

In one embodiment, temperature sensors 2570 may be disposed on the waveguide 2508. The temperature sensors 2570 may be a thermocouple probe having thermocouple wires twisted together and soldered together at a junction. The temperature sensors 2570 may provide temperature feedback to the feedback mechanism 2574, which may then adjust the power delivered to the distal end of the gun 2500 in response to the temperature readings. In other words, when the temperature reaches the desired level for the selected function, indicating a desired tissue condition, a signal is provided to a control unit or the user, at which time the energy supply is switched off or attenuated. The feedback signal may, for example, provide a visual, audible or tactile signal to a user, and/or may provide instructions to a control unit to automatically readjust the energy supply to the tissue. Of course, such steps may be taken in regards to any parameter that is being sensed and measured by the gun 2500.

In addition to temperature feedback, the gun 2500 may also be configured to interrogate tissue to determine various tissue properties. In one embodiment, the transducer 2516 is energized to produce an ultrasound interrogation pulse (e.g., A-mode ultrasound). The interrogation pulse may be transmitted periodically during the procedure or after the commencement thereof to determine, for instance, the thickness or type of tissue being grasped at the distal end of the gun 2500. The interrogation pulse may be of different frequency and amplitude than the treatment pulses used to seal tissue.

In summary, the feedback mechanism 2574 may supply a variety of information related to one or more parameters to the ultrasonic surgical instrument or gun 2500. According to the information received by the ultrasonic surgical instrument or gun 2500, the one or more parameters may be adjusted based on load variations created by the tissue. The load variations include resonance or vibration patterns located across a length of the instrument or gun 2500. Specifically, the load variations may be located and measured at the cutting element (blade 2504), the clamp member 2576, the handle member (handle 2514) or the ultrasonic transmission member (waveguide 2508). Additionally, the information may include ultrasonic wave information, where the ultrasonic wave information is used to adjust one or more power levels of waves applied to the tissue. The information received by the gun 2500 may be automatically provided in real-time during electrical activation of the gun 2500 for enabling automatic adjustment of the one or more parameters. Also, the energy applied to the tissue may be continuously and automatically regulated as a function of the load variations.

The ultrasonic transmission member or waveguide 2508 may be constructed from titanium, where the titanium expands/elongates and contracts/shrinks along a longitudinal direction during electrical activation of the gun 2500. Of course, the waveguide 2508 may be fabricated from aluminum, steel, or any other suitable material. In the example embodiments, when the titanium member is heated by an electric current, the titanium expands and when cooled the titanium returns to its original dimensions. The variation of the titanium dimensions may be one parameter sensed, measured, and adjusted by the gun 2500. Thus, energy applied to the distal end of the gun 2500 may be adjusted based on the expansion and contraction of the materials used to fabricate and/or manufacture the components/elements of the gun 2500. Of course, one skilled in the art may contemplate a sensing, measuring, and adjusting a plurality of different variables in order to determine load differential due to tissue application.

Figure 11:
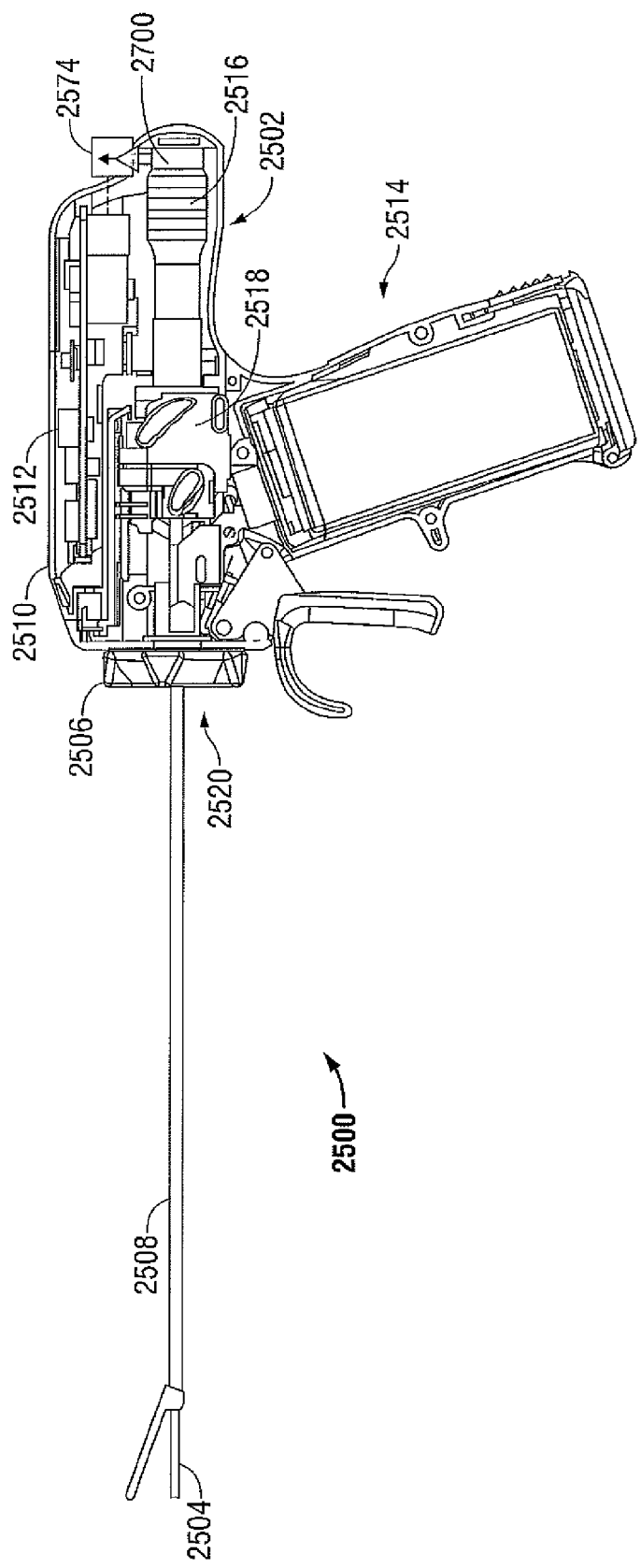
FIG. 11 is a side, elevational view of an handle with the left-side shell removed to show a transducer, generator, and load cell, in accordance with an example embodiment of the present disclosure.
Figure 12:
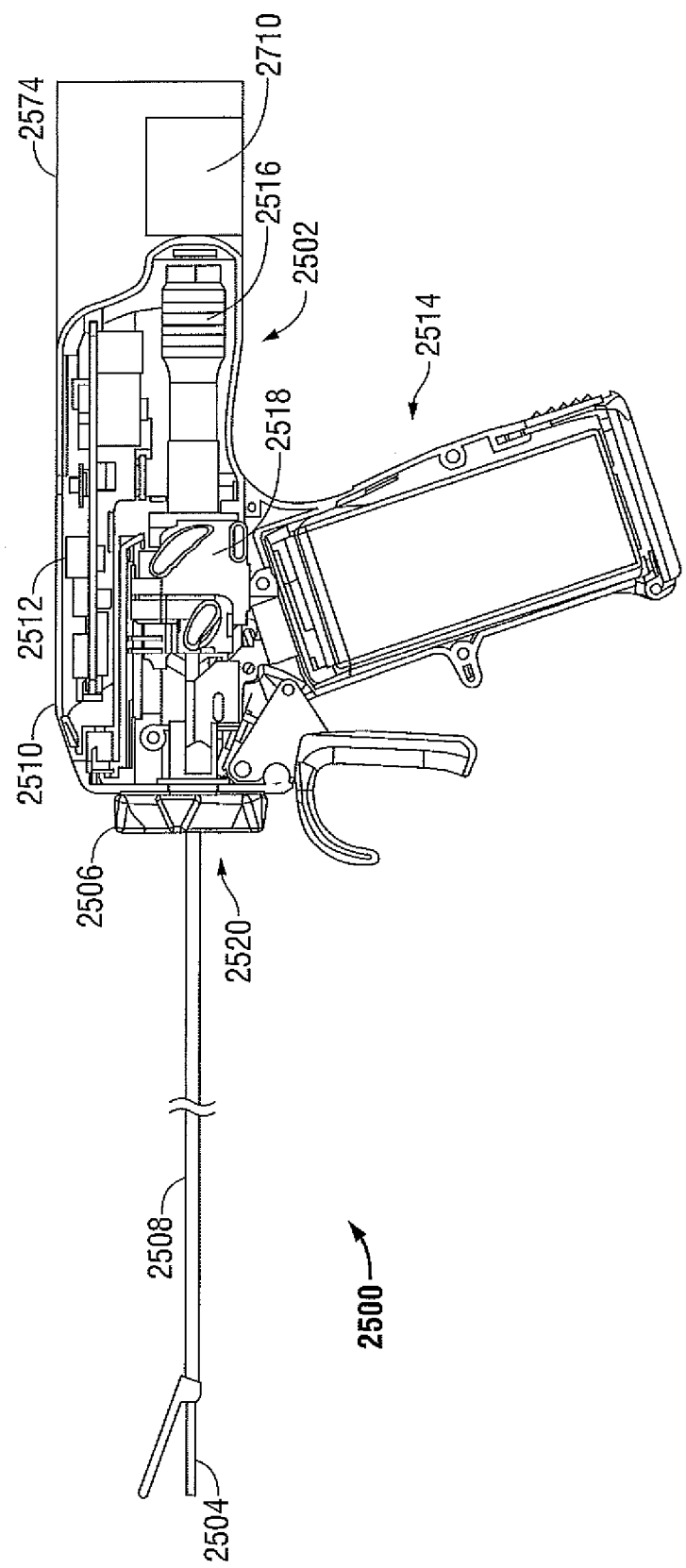
FIG. 12 is a side, elevational view of an handle with the left-side shell removed to show a transducer, generator, and laser interferometry configuration, in accordance with an example embodiment of the present disclosure.
Figure 13:
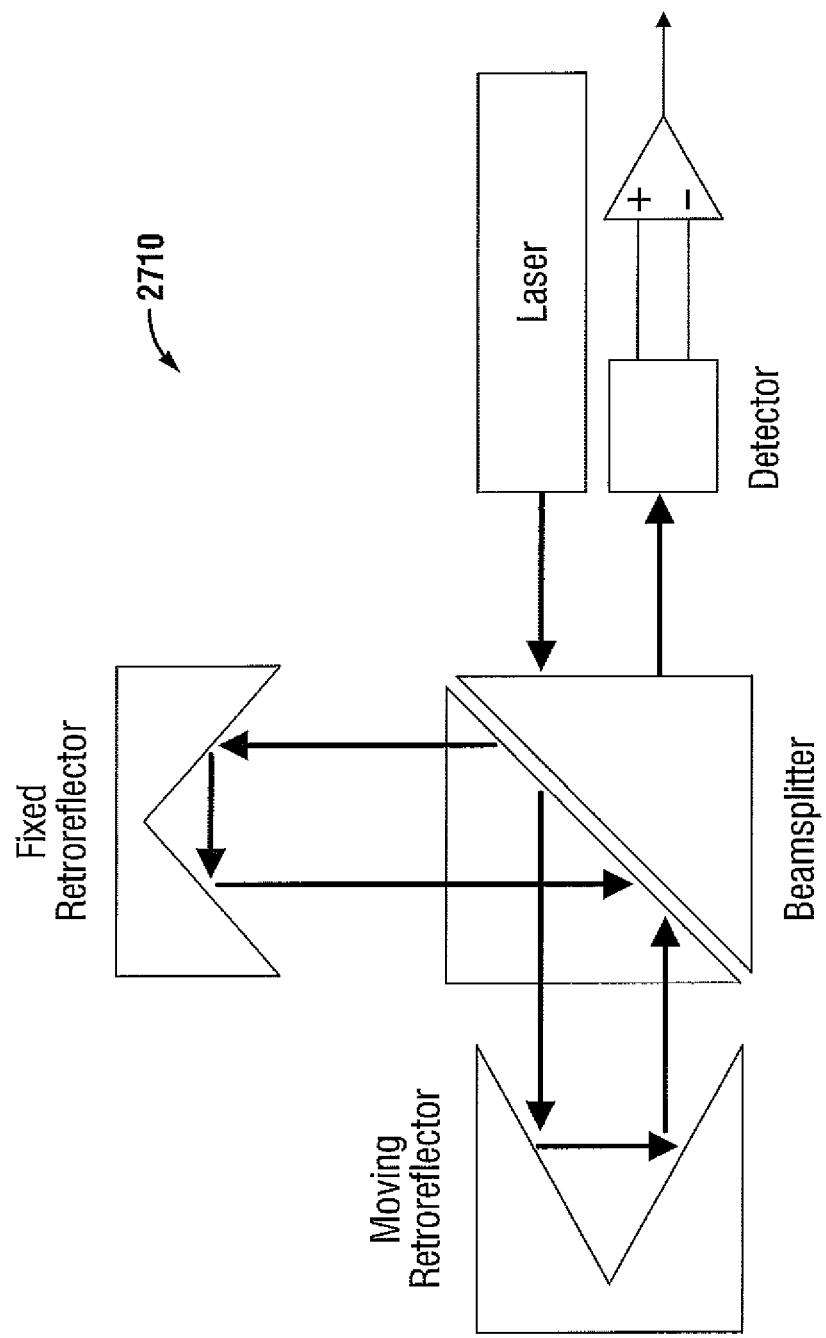
FIG. 13 is a laser interferometer as shown in FIG. 12, in accordance with an example embodiment of the present disclosure.

Moreover, the load variations may be measured by load cells 2700 (as shown in FIG. 11) or the load variations may be measured by a laser interferometry configuration 2710 (as shown in FIGS. 12 and 13). A load cell 2700 may be a type of transducer that converts physical force into measurable, quantifiable electric energy. Because of the various types of load cells 2700 needed to operate different pieces of machinery, there are many configurations, but the most popular are of the strain gauge variety. This is a device which measures strain, and then transfers that force into electric energy which manifests as measurement for operators of the machinery. One skilled in the art may envision using hydraulic, pneumatic, and/or strain gauge load cells 2700 in accordance with the example embodiments of the present disclosure. Additionally, interferometry is a technique of diagnosing the properties of two or more lasers or waves by studying the pattern of interference created by their superposition. The instrument used to combine the waves together is called an interferometer. Interferometry makes use of the principle of superposition to combine separate waves together in a way that causes the result of their combination to have some meaningful property that is diagnostic of the original state of the waves. Both the load cells 2700 and the laser interferometry configuration 2710 may be located within the handle 2514. Of course, the load cells 2700 and the laser interferometry configuration 2710 may be located on any external or in any internal location of the gun 2500 (e.g., such as in the main body of the gun 2500).

The sensing methods (e.g., 2700 and 2710) described above may be based on analyzing the interferometric features associated with the reverberation of ultrasound in a medical instrument, such as the gun 2500. Reflected light from a continuous source (not shown) may be detected by the interferometer to probe the ultrasonic vibrations across the various portions of the gun 2500. Motions or vibrations or waves along the gun 2500 at ultrasonic frequencies generate a shift in the frequency of the continuous light source. This modulation of the continuous light source frequency may be monitored by the interferometer and may be converted to a signal that is recorded and processed by, for example, a processor or a computer. Signal processing may involve identifying the resonance frequencies of ultrasonic motion across different surfaces of the gun 2500. These resonant frequencies, in conjunction with some physical properties of the material of the gun 2500 may be used to determine, for example, whether to automatically shut off the gun 2500. Additionally, measurements of the intensity of the scattered laser light at the output of the interferometer may be used to generate a pre-stabilization signal. Also, the intensity of the scattered laser light at the input of the interferometer may be measured to generate a reference signal. These measurements may be used to electronically generate a ratio signal indicative of the ratio between the reference signal and the pre-stabilization signal and processing of the ratio signal may be used to generate a final stabilization signal which is used to ensure a proper operation of the interferometer. Thus, the phase of the returned ultrasound signals could be used to perform interferometry to locate any changes in one or more desired parameters to be monitored.

Any type of interferometer known in the art may be used. For example, the interferometer used in embodiments of the present disclosure may include, but not be limited to, time delay interferometers (TD-LCI), such as, scanning Michelson interferometers and autocorrelators, and optical frequency domain interferometers (OFDI), such as, spectral domain low-coherence interferometers, and these interferometers may be used to detect interference between one or more reference optical signals and one or more backscattered sample optical signals or birefringence caused by the sample. Such optical probes may be embedded in the gun 2500 or may be located on the outer surfaces of the proximal end of the gun 2500.

Moreover, the sensing mechanism may be used as a safety mechanism for the gun 2500. For example, the sensing mechanism may sense that no tissue or no object is found between the jaws of the blade 2504 and automatically shut off operation of the gun 2500. The advantages of using load cells 2700 or an interferometer 2710 as discussed with reference to FIGS. 11-13 may include (1) calibration of the interferometric apparatus in real-time, (2) automatically stabilizing frequencies across a medical instrument, and/or (3) providing an improved sensing method and apparatus useful for ultrasonic non-destructive testing of the medical instrument.

Concerning feedback mechanism, several types of feedback systems may be used. For example, a pressure detector or strain gauge may be used to detect tissue presence, status or type. Electrical parameters may be used to sense and determine the variation in load conditions on the cutting element as acoustical impedance is related to the system impedance of the generator and instrument. In such a system, either phase differences of voltage and current or magnitude ratios of voltage and current supplied to the transducer 2516, are used to make this determination. In addition to the feedback mechanism 2574, a method of performing the present disclosure may include the steps of supplying ultrasonic energy to tissue, supplying high-frequency electrical energy to tissue, sensing and measuring one or more tissue parameters or waveguide parameters, and altering or readjusting the output of the ultrasonic generator in response to measured tissue or waveguide parameters in a continuous and automatic manner in real-time.

It is also contemplated that operation of gun 2500 may be automatically controlled through the use of a computer, for example, in a wireless manner. In one alternative embodiment of the presently disclosed system, a computer (not explicitly shown) may receive data from the sensors 2570 positioned on the blade 2504 of the gun 2500. As discussed above, sensors 2570 may be provided to monitor different characteristics of the tissue being operated upon including, inter alia, temperature and/or ultrasonic or electrical impedance. The computer may include circuitry to process an analog signal received from the sensors 2570 and to convert the analog signal to a digital signal. This circuitry may include means to amplify and filter the analog signal. Thereafter, the digital signal may be evaluated and operation of the gun 2500 (e.g., application of energy) may be modified to achieve the desired effect in or on the tissue and prevent damage to surrounding tissue. Thus, all the information gathered by the sensors 2570 may be wirelessly transferred to the computer in a local or remote location for further processing (e.g., tracking and recording historical information/data), as discussed below.

As stated, the information gathered (e.g., from the computer described above) may be stored separately in a local or remote database for further processing. This may be a unique database designed solely for storing and analyzing such different types of information/data. Also, once a history of adjustments are collected and stored for each of the one or more parameters, that history may be evaluated in the future for determining which parameter modifications achieved the best desired results for the surgeon. In other words, the parameter changes that took place (past changes) may be stored and later compared against each other and ranked in order of best achieved results.

In addition to the advantages of reduced cost, reduced size, elimination of a tethering cord for supplying power and carrying signals, real-time feedback, and automatic energy application adjustment, the present disclosure provides unique advantages for maintaining a sterile environment in an operating or other environment. More specifically, in example embodiments of the present disclosure, the handle includes an aseptic seal. An "aseptic" seal, as used herein, means a seal that sufficiently isolates a compartment (e.g., inside the handle) and components disposed therein from a sterile field of an operating environment into which the handle has been introduced so that no contaminants from one side of the seal are able to transfer to the other side of the seal.

Although specific embodiments of the present disclosure have been disclosed, those having ordinary skill in the art will understand that changes may be made to the specific embodiments without departing from the spirit and scope of the disclosure. The scope of the disclosure is not to be restricted, therefore, to the specific embodiments, and it is intended that the appended claims cover any and all such applications, modifications, and embodiments within the scope of the present disclosure.

From the foregoing, and with reference to the various figure drawings, those skilled in the art will appreciate that certain modifications may also be made to the present disclosure without departing from the scope of the same. While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a clamping mechanism configured to clamp tissue and adapted to apply energy to tissue;
   a laser interferometer operably coupled to the clamping mechanism and configured to sense properties of tissue clamped by the clamping mechanism;
   a feedback mechanism coupled to the laser interferometer and configured to supply information relating to the sensed properties of tissue; and
   a controller configured receive the information relating to the sensed properties of tissue and to selectively control the application of energy from the clamping mechanism to tissue based on the information relating to the sensed properties of tissue.

2. The surgical instrument according to claim 1, wherein the sensed properties of tissue include at least one of tissue impedance, tissue type, tissue clarity, and tissue compliance.

3. The surgical instrument according to claim 1, wherein the laser interferometer is configured to sense an intensity of scattered laser light at an output of the interferometer and an intensity of scattered laser light at an input of the interferometer.

4. The surgical instrument according to claim 1, wherein the laser interferometer is configured to detect interference between one or more reference optical signals and one or more backscattered tissue optical signals.

5. The surgical instrument according to claim 1, wherein the controller is configured to selectively control the application of energy from the clamping mechanism to tissue to coagulate tissue.

6. The surgical instrument according to claim 1, wherein the controller is configured to selectively control the application of energy from the clamping mechanism to tissue to cut tissue.

7. The surgical instrument according to claim 1, further comprising a handle assembly operable to effect clamping of tissue with the clamping mechanism.

8. The surgical instrument according to claim 1, wherein the controller automatically controls the application of energy from the clamping mechanism to tissue based on the information relating to the sensed properties of tissue.

9. The surgical instrument according to claim 8, wherein the clamping mechanism of the ultrasonic surgical instrument includes a clamp member and an ultrasonically-actuated element.

10. The surgical instrument according to claim 1, wherein the feedback mechanism supplies the information relating to the sensed properties of tissue to the controller in real-time.

11. The surgical instrument according to claim 1, wherein the feedback mechanism includes one of an open feedback loop and a closed feedback loop.

12. The surgical instrument according to claim 1, wherein the surgical instrument is an ultrasonic surgical instrument.

13. A method of applying energy to tissue via a surgical instrument, the method comprising the steps of:
    positioning a clamping mechanism adjacent tissue;
    moving the clamping mechanism to clamp tissue;
    applying energy from the clamping mechanism to tissue grasped therebetween;
    using a laser interferometer to sense properties of tissue clamped by the clamping mechanism;
    supplying information related to the sensed properties of tissue to a controller via a feedback mechanism operably coupled to the laser interferometer; and
    selectively controlling the supply of energy from the clamping mechanism to tissue based on the information related to the sensed properties of tissue.

14. The method according to claim 13, wherein sensed properties of tissue include at least one of tissue impedance, tissue type, tissue clarity, and tissue compliance.

15. The method according to claim 13, wherein the step of using a laser interferometer to sense properties of tissue includes sensing an intensity of scattered laser light at an output of the interferometer and an intensity of scattered laser light at an input of the interferometer.

16. The method according to claim 13, wherein the step of using a laser interferometer to sense properties of tissue includes detecting interference between one or more reference optical signals and one or more backscattered tissue optical signals.

17. The method according to claim 13, wherein the step of controlling the supply of energy from the clamping mechanism to tissue based on the information related to the sensed properties of tissue is performed automatically by a controller.

18. The method according to claim 13, wherein the supply of energy from the clamping mechanism to tissue is controlled via one of an open feedback loop and a closed feedback loop.

19. The method according to claim 13, wherein the application of energy from the clamping mechanism to tissue is used to coagulate tissue.

20. The method according to claim 13, wherein the application of energy from the clamping mechanism to tissue is used to cut tissue.

* * * * *